United States Patent [19]

Ikuzawa et al.

[11] Patent Number: 5,008,243
[45] Date of Patent: Apr. 16, 1991

[54] PHARMACEUTICAL COMPOSITION CONTAINING A GLYCOPROTEIN

[75] Inventors: Masanori Ikuzawa; Yoshiharu Oguchi; Kenichi Matsunaga, all of Tokyo; Noriyuki Toyoda, Sagamihara; Takao Furusho, Tokyo; Takayoshi Fujii, Tokyo; Chikao Yoshikumi, Tokyo, all of Japan

[73] Assignee: Kureha Kagaku Kogyo Kabushiki Kaisha, Tokyo, Japan

[21] Appl. No.: 285,664

[22] Filed: Dec. 16, 1988

Related U.S. Application Data

[60] Division of Ser. No. 898,900, Aug. 22, 1986, Pat. No. 4,820,689, which is a continuation of Ser. No. 637,831, Aug. 6, 1984, abandoned.

[30] Foreign Application Priority Data

| Aug. 11, 1983 | [JP] | Japan | 58-147231 |
| Aug. 11, 1983 | [JP] | Japan | 58-147232 |
| Aug. 11, 1983 | [JP] | Japan | 58-147233 |
| Aug. 11, 1983 | [JP] | Japan | 58-147234 |
| Aug. 11, 1983 | [JP] | Japan | 58-147235 |
| Aug. 11, 1983 | [JP] | Japan | 58-147236 |
| Aug. 11, 1983 | [JP] | Japan | 58-147237 |
| Aug. 11, 1983 | [JP] | Japan | 58-147238 |
| Aug. 11, 1983 | [JP] | Japan | 58-147239 |
| Aug. 11, 1983 | [JP] | Japan | 58-147240 |
| Aug. 11, 1983 | [JP] | Japan | 58-147241 |

[51] Int. Cl.$^5$ .................................................. A61K 37/02
[52] U.S. Cl. ................................. 514/8; 435/71.1; 435/911
[58] Field of Search .................... 514/8; 536/55.1; 435/911, 71.1

[56] References Cited

U.S. PATENT DOCUMENTS

| 3,929,994 | 12/1975 | Hirsch et al. | 514/8 |
| 4,140,578 | 2/1979 | Yoshikumi et al. | 536/55.1 |
| 4,202,885 | 5/1980 | Asano et al. | 536/55.1 |
| 4,202,969 | 5/1980 | Ueno et al. | 536/55.1 |
| 4,229,570 | 10/1980 | Ueno et al. | 536/55.1 |
| 4,268,505 | 5/1981 | Yoshikumi et al. | 536/55.1 |

OTHER PUBLICATIONS

Chem. Absts., vol. 87, 1977, No. 21138n.
Stedman's Medical Dictionary, 24th Edition, p. 473, 1982.
Schiri et al., Chem. Abstracts, vol. 66, 9877g (1964).
Rereno et al., Chem. Abstracts, vol. 66, 16570f (1964).

Primary Examiner—Jacqueline Stone
Attorney, Agent, or Firm—Oblon, Spivak, McClelland, Maier & Neustadt

[57] ABSTRACT

Disclosed herein is a pharmaceutical composition having antirheumatic activity, antithrombotic activity, analgetic activity, antipyretics activity, anti-hyperlipemic activity and anti-inflammatory activity and activities of reducing the level of blood sugar, raising the coronary blood flow, improving the capability of deformation of erythrocytes, reducing the blood pressure, ameliorating proteinuria and proteinemia and regulating production or metabolism of prostaglandins in a mammal in dosage unit form, which comprises a dosage effective to produce said activities of a glycoprotein having a molecular weight of 5000 to 300,000 as determined by ultracentrifugal method and about 18 to 38% by weight of proteins, produced by culturing a basidiomycetous fungal species belonging to the genus Coriolus, extracting the thus proliferated mycelia or fruit bodies with hot water or aqueous alkali solution and removing low molecular weight substances having a molecular weight of less than 5000 from the extract.

13 Claims, 6 Drawing Sheets

PHARMACEUTICAL COMPOSITION CONTAINING A GLYCOPROTEIN

This is a division of application Ser. No. 06/898,600, filed Aug. 22, 1986, now U.S. Pat. No. 4,820,689, which is a continuation of application Ser. No. 06/637,831 filed Aug. 6, 1984, now abandoned.

BACKGROUND OF THE INVENTION

The present invention relates to a pharmaceutical composition having antirheumatic activity, antithrombotic activity, analgetic activity, antipyretic activity, anti-hyperlipemic activity and anti-inflammatory activity and activities of reducing the level of blood sugar, raising the coronary blood flow, improving the capability of deformation of erythrocytes, reducing the blood pressure, ameliorating proteinuria and proteinemia and regulating production or metabolism of prostaglandins in a mammal, containing a glycoprotein derived from a basidiomycetous fungus belonging to the genus Coriolus, for instance, Coriolus versicolor (Fr.) Quél., as an active ingredient. The glycoprotein derived from Coriolus versicolor (Fr.) Quél. [FERM-P No. 2412 (ATCC 20547)] has been already supplied to the public as an anti-tumour drug under the trade mark of Krestin.

Since the glycoprotein is low in mammalian toxicity and does not disturb the intestinal microflora, the pharmaceutical composition containing the glycoprotein as an active ingredient can be administered for a long time period. In addition, the glycoprotein is quite free of the fear of causing malformation and/or allergic reaction and accordingly, the glycoprotein is an extremely safe substance.

The active ingredient, the glycoprotein, of the pharmaceutical composition according to the present invention is a publicly known substance, and as has been disclosed in Japanese Patent publications Nos. 17149/1971, 36322/1976, 14274/1981, 14276/1981 and 39288/1981, the glycoprotein is obtained by culturing a basidiomycetous fungal species belonging to the genus Coriolus, extracting the thus proliferated mycelia or fruit bodies with hot water or an aqueous alkali solution, and removing low molecular weight substances having a molecular weight of less than 5000 and the thus obtained substance as an extract contains from about 18 to 38% by weight of proteins and shows a molecular weight of from 5,000 to 300,000 as determined by ultracentrifugal method.

The glycoprotein derived from the mycelia of Coriolus versicolor (Fr.) Quél. is liver brown in color and has a nitrogen content of 2 to 8%, in many cases 3 to 6%. Various color reaction tests on the glycoprotein according to the present invention gave the results as shown below.

| | |
|---|---|
| α-naphthol sulfuric acid reaction (Molish's reaction) | Purple |
| Indole sulfuric acid reaction (Dische's reaction) | Brown |
| Anthrone sulfuric acid reaction | Greenish blue |
| Phenol sulfuric acid reaction | Brown |
| Tryptophane sulfuric acid reaction | Purplish brown |
| Lowry-Folin process | Blue |
| Ninhydrin reaction after hydrochloric acid hydrolysis | Greenish blue |

The molecular weight of the glycoprotein according to the present invention is 5000 to 300,000 as measured according to an ultracentrifugal method. The glycoprotein according to the present invention contains about 18 to 38% by weight of proteins.

The saccharide moiety of the glycoprotein of the present invention consists mainly of β-D-glycan and the structure of the glycan moiety is a branched one containing 1→3, 1→4 and 1→6 bondings. Of the amino acids forming the protein moiety of the glycoprotein, the amount of acidic amino acids such as aspartic acid, glutamic acid, etc. and that of neutral amino acid such as valine, leucine, etc. are relatively large, and the amount of basic amino acids such as lysine, arginine, etc. is relatively small. The glycoprotein is soluble in water and almost insoluble in hexane, benzene, chloroform, methanol and pyridine. The glycoprotein slowly decomposes at a temperature around 120° C. when it is heated.

As will be seen in Table 1, the mammalian toxicity of the glycoprotein of the present invention is extremely low, and it hardly causes any side effects on animals. Namely, it is known to be a very safe substance to living bodies.

TABLE 1

| Animal species | Route of administration | $LD_{50}$(mg/kg) Female | $LD_{50}$(mg/kg) Male |
|---|---|---|---|
| Mouse | intravenous | >1300 | >1300 |
| Strain | subcutaneous | >5000 | >5000 |
| ICR-JCL | intraperitoneal | >5000 | >5000 |
| | oral | >20000 | >20000 |
| Rat | intravenous | >600 | >600 |
| Strain | subcutaneous | >5000 | >5000 |
| Donryu | intraperitoneal | >5000 | >5000 |
| | oral | >20000 | >20000 |

The mice used in the test for finding the above-mentioned acute toxicity value ($LD_{50}$mg/kg) were of the strain ICR-JCL, 4 to 5 weeks after birth, and body weight of 21 to 24 g. The rats used in the same test were of the strain Donryu, 4 to 5 weeks after birth, and body weight of 100 to 150 g. The glycoprotein was dissolved in a physiological saline and administered via each route shown in Table 1. After administration, observation on the general symptoms, mortality and body weight of each of the thus treated animals were carried out for 7 days, and then they were sacrificed to be subjected to autopsy.

As are shown in Table 1, no case of death was found both on the mice and the rats even at the maximum dosage which could be given and accordingly, the glycoprotein of the present invention is extremely safe for living body to the extent that the value of $LD_{50}$ could not be actually determined.

As a result of examining the physiological and pharmaceutical properties of the glycoprotein derived from a basidiomycetous fungus belonging to the genus Coriolus, it has been found out that the glycoprotein shows antirheumatic activity, antithrombotic activity, analgetic activity, antipyretic activity, anti-hyperlipemic activity and anti-inflammatory activity and activities of reducing the level of blood sugar, raising the coronary blood flow, improving the capability of deformation of erythrocytes, reducing the blood pressure, ameliorating proteinuria and proteinemia and regulating production or metabolism of prostaglandins in a mammal, as well as the anti-tumour activity, and based on the findings, the present inventors have attained the present invention.

SUMMARY OF THE INVENTION

In the first aspect of the present invention, there is provided a pharmaceutical composition having antirheumatic activity, antithrombotic activity, analgetic activity, antipyretic activity, anti-hyperlipemic activity and anti-inflammatory activity and activities of reducing the level of blood sugar, raising the coronary blood flow, improving the capability of deformation of erythrocytes, reducing the blood pressure, ameliorating proteinuria and proteinemia and regulating production or metabolism of prostaglandins in a mammal in dosage unit form, which comprises a dosage effective to produce said activities of a glycoprotein having a molecular weight of 5000 to 300,000 as determined by ultracentrifugal method and about 18 to 38% by weight of proteins, produced by culturing a basidiomycetous fungal species belonging to the genus Coriolus, extracting the thus proliferated mycelia or fruit bodies with hot water or aqueous alkali solution and removing low molecular weight substances having a molecular weight of less than 5000 from the extract.

In the second aspect of the present invention, there is provided a method for the treatment of diabetes mellitus, rheumatism, ischemic heart diseases, ischemic cerebral diseases, hypertension, thrombosis, pains due to the accentuation of central nerve, pyrexia due to accentuation of central nerve, hyperlipemia, inflammatory diseases and nephrotic syndrome, which comprises administering to a mammal suffering from diabetes mellitus, rheumatism, ischemic heart diseases, ischemic cerebral diseases, hypertension, thrombosis, pains due to the accentuation of central nerve, pyrexia due to accentuation of central nerve, hyperlipemia, inflammatory diseases and nephrotic syndrome an effective amount of a glycoprotein having a molecular weight of 5000 to 300,000 as determined by ultracentrifugal method and about 18 to 38% by weight of proteins, produced by culturing a basidiomycetous fungal species belonging to the genus Coriolus, extracting the thus proliferated mycelia or fruit bodies with hot water or aqueous alkali solution and removing low molecular weight substances having a molecular weight of less than 5000 from the extract.

In the third aspect of the present invention, there is provided a method for regulating the production and metabolism of prostaglandins in a mammal, which comprises administering an effective amount of a glycoprotein having a molecular weight of 5000 to 300,000 as determined by ultracentrifugal method and about 18 to 38% by weight of proteins, produced by culturing a basidiomycetous fungal species belonging to the genus Coriolus, extracting the thus proliferated mycelia or fruit bodies with hot water or aqueous alkali solution and removing low molecular weight substances having a molecular weight of less than 5000 from the extract.

BRIEF EXPLANATION OF DRAWINGS

Of the attached drawings.

DETAILED DESCRIPTION OF THE INVENTION

Figure 1:
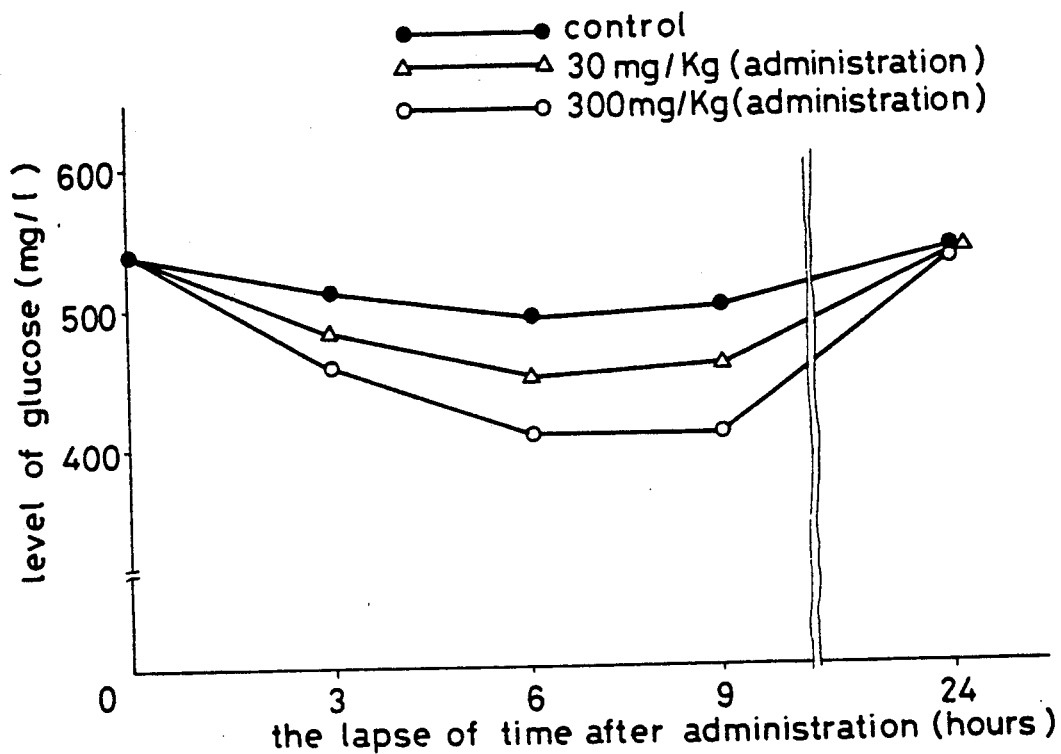
FIG. 1 shows the transition of the level of glucose in the blood of the rat experimentally made to be in a morbid state of showing a high level of sugar both in the urine and the blood, with the lapse of time.

The glycoprotein according to the present invention shows antirheumatic activity, antithrombotic activity, analgetic activity, antipyretic activity, anti-hyperlipemic activity and anti-inflammatory activity and activities of reducing the level of blood sugar, raising the coronary blood flow, improving the capability of deformation of erythrocytes, reducing the blood pressure, ameliorating proteinuria and proteinemia and regulating production or metabolism of prostaglandins in a mammal. The glycoprotein according to the present invention is used for the treatment of diabetes mellitus, rheumatism, ischemic heart diseases, ischemic cerebral diseases, hypertension, thrombosis, pains due to the accentuation of central nerve, pyrexia due to accentuation of central nerve, hyperlipemia, inflammatory diseases and nephrotic syndrome, and for regulating the production and metabolism of prostaglandins.

The followings are the pharmacological properties of the glycoprotein according to the present invention.

(1) Activity of reducing the level of blood sugar

The glycoprotein according to the present invention was orally administered at a dose rate of 30 to 300 mg/kg to the rat artificially made to diabetes mellitus by administration of streptozocin. As a result, the reduction of the level of blood sugar by 50 to 100 mg/dl was observed.

(2) Antirheumatic activity

In the case where the glycoprotein according to the present invention was administered to a patient suffering from rheumatism, improvements of both the pain and the grasping power were observed on the patient. In addition, in the animal experiment of rats, it was found that the glycoprotein had an anti-adjuvant arthritic activity. Namely, the glycoprotein of the present invention has an activity as an antirheumatic agent.

(3) Activity of raising the coronary blood flow

The glycoprotein according to the present invention shows an activity of raising the coronary blood flow and accordingly, the glycoprotein is useful as an improving agent of ischemic heart diseases. Namely, when the glycoprotein was injected into the upper artery of a cardiopulmonary specimen prepared from a normal beagle, an increase of the coronary blood flow was observed, and the effectiveness of the glycoprotein as an improving agent of ischemic heart diseases was shown.

The glycoprotein according to the present invention is effective as an agent for ameliorating ischemic heart diseases due to the activity of increasing the coronary blood flow. Namely, the pharmaceutical composition according to the present invention is effective in treating the several types of ischemic heart diseases such as coronary arteriosclerosis, acute- and chronic myocardial infarction, stable- or unstable angina pectoris, arrhythmia, heart failure, etc.

(4) Activity of improving the capability of deformation of erythrocytes

On the erythrocytes of the animal to which the glycoprotein according to the present invention was administered, the reduction of rate of hemolysis against the mechanical hemolytic action, in other words, the improvement of the capability of deformation of the erythrocytes was observed. The blood flow in the cerebral ischemic state was microcirculation, and since an activity of improving the capability of deformation of the erythrocytes was recognized in the glycoprotein according to the present invention, it was elucidated that the active ingredient, the glycoprotein, was able to facilitate the blood circulation. In addition, the glycoprotein is active in inhibiting the death of experimental animal due to thrombosis caused by arachidonic acid given to the animal.

The glycoprotein is useful as an agent for ameliorating ischemic cerebral diseases because of both the activity of improving the capability of deformation of erythrocytes and the activity of inhibiting the death due to thrombosis. The pharmaceutical composition for ameliorating ischemic cerebral diseases according to the present invention is effective in treating cerebral thrombosis or ischemic diseases accompanying the cerebral infarction due to arteriosclerosis.

(5) Activity of reducing the blood pressure

As a result of the experimental tests wherein the glycoprotein of the present invention was orally administered at dose rates in a range of from 30 to 300 mg/kg to SHR (spontaneous hypertensive rats), which were used broadly as the model of human essential hypertension, and their blood pressures were measured with the lapse of time by non-operative method, a reduction of the blood pressure was observed in a range of from 15 to 25 mmHg. Accordingly, the activity of the glycoprotein in reducing the blood pressure was recognized.

(6) Antithrombotic activity

The antithrombotic activity of the glycoprotein according to the present invention is explained as follows.

(i) Activity in inhibiting the aggregation of platelets

In the case where collagen, etc. which is present beneath the endotheliucomes to be exposed to blood flow due to arteriosclerosis and injury of the intima, the platelets adhere to the part and then, aggregation of the thus adhered platelets occurs. The aggregation of the platelets due to collagen causes the release of adenosine-diphosphoric acid(ADP), serotonin, etc. from the dense body of the thrombocyte. ADP has a strong activity of aggregating the platelets and accordingly, ADP causes an irreversible second aggregation.

As is seen in Example 10, an activity of inhibiting the aggregation of platelets is seen in the glycoprotein according to the present invention.

(ii) Activity in inhibiting the death due to thromboembolism

In the case where a platelets-aggregating substance such as ADP or water-soluble collagen is intravenously administered to a mouse, the platelets are aggregated in the blood flow to clog the capillary blood vessel resulting finally in pulmonary embolism, and the rat dies within 5 min.

In the case where the glycoprotein of the present invention was administered before the injection of the platelets-aggregating substance, an effect of inhibiting the death due to thromboembolism (refer to Example 11) was observed.

Namely, the glycoprotein according to the present invention is effective as an antithrombotic agent because of the activities of inhibiting the aggregation of platelets and of inhibiting the death due to aggregation of platelets.

(7) Analgetic and antipyretic activity

The analgetic- and antipyretic activity of the glycoprotein according to the present invention is explained as follows.

(i) Analgetic activity

As a result of examination on the analgetic activity of the glycoprotein as the active ingredient of the pharmaceutical composition of the present invention by the mechanical stimulation (by pressure) method and chemical stimulation method while using mice as the experimental animal, it was found that the oral administration of 1000 mg/kg of the glycoprotein caused the raise of the pressure at the time of exhibiting of the pseudo-escape reaction, the elongation of the time until the appearance of the pseudo-escape reaction and the reduction of writhing number.

(ii) Antipyretic activity

As a result of examination on the antipyretic activity of the glycoprotein as the active ingredient of the pharmaceutical composition of the present invention by the method of subcutaneous administration of beer yeast while using rats as the experimental animal, the oral administration of 1000 mg of the glycoprotein per kg body weight of the rat caused a pyrexia-suppressing effect, i.e., a reduction of body temperature to level of body temperature of the rat not treated with beer yeast.

(8) Anti-hyperlipemic activity

The anti-hyperlipemic activity of the glycoprotein according to the present invention will be explained as follows.

It has been known that the patient suffering from hyperlipemia also suffers from hypercholesterolemia and frequently is complicated by arteriosclerosis praecox. Accordingly, the treatment of hyperlipemia means not only the prevention and inhibition of arteriosclerosis but also the improvement thereof. Hitherto, the treatment of hyperlipemia is carried out for the purpose of repressing the synthesis of cholesterol, accelerating catabolism and excretion of cholesterol and repressing the absorption of cholesterol, and the anti-hyperlipemic pharmaceutical compositions now in use exhibit their activity via the above-mentioned functional mechanisms.

On the other hand, the glycoprotein according to the present invention reduces the high level of the lipids within blood via a novel functional mechanism.

Namely, in recent years, it has been found that the principal cause of hyperlipemia is the deficiency and the functional reduction of low density lipoprotein (hereinafter referred to as LDL)-receptor, and it has come to be considered that the amelioration of the acatastatic LDL receptor is the substantial and ideal treatment of hyperlipemia.

The pharmaceutical composition of the present invention is, in that sense, a new anti-hyperlipemic pharmaceutical composition which raise the level of LDL receptor in the patient's body, thereby reducing the lipids in the blood of the patient without causing side effect.

(9) Anti-inflammatory activity

The glycoprotein according to the present invention has an activity of repressing the edema due to carragheenin, that of repressing granuloma, and that of repressing adjuvant arthritis and accordingly, the pharmaceutical composition essentially containing the glycoprotein as an active component is useful as an anti-inflammatory agent.

These activities will be explained as follows.

(i) Activity of repressing the edema due to carragheenin

Following the method of Van Arman et al. (1963), the activity of repressing the occurrence of the edema due to carragheenin was examined on rats. The rate of repressing the occurrence of the carragheenin-edema was 50.6% when 1000 mg/kg of the glycoprotein was orally administered once to the rat (refer to Example 14).

(ii) Activity of repressing the occurrence of granuloma

Following the method of Winter et al. (1963), the activity of the present glycoprotein in repressing the granuloma was examined on rats. The rate of repressing granuloma due to cotton wool by the daily oral administration of 1000 mg/kg for 7 days of the glycoprotein was 49.9% (refer to Example 14).

(iii) Activity of repressing exudation

Following the method of Baris et al. (1965), the activity of the present glycoprotein in repressing exudation into the subcutaneously inserted pouch in the back of a rat containing air and croton oil was examined. Daily oral administration of 1000 mg/kg of the glycoprotein for 5 days inhibited the extravasation to the extent of 39.7%.

(iv) Activity of repressing the adjuvant-arthritis due to bacteria

Following the method of Fujiwara et al. (1971), the rate of repressing the occurrence of the adjuvant arthritis was examined by the daily oral administration of 1000 mg/kg of the glycoprotein for 7 days. The glycoprotein showed an activity of repressing arthritis in several months.

(10) Activity of ameliorating proteinuria and proteinemia

Since in the experimental case of rats exhibiting the nephrose-like symptoms and also in the clinical case of a patient suffering from lupus nephritis, administration of the glycoprotein according to the present invention caused the reduction of the level of proteins in the urine of the animal and the patient, it has been confirmed that the glycoprotein has an activity of ameliorating proteinuria and proteinemia and is useful as an active ingredient of the pharmaceutical composition for ameliorating nephrotic syndrome.

(11) Activity of regulating production or metabolism of prostaglandins

The glycoprotein according to the present invention participates the regulation of PGs such as PGA, PGB, PGC, PGD, PGE, PGF, PGG, PGH, PGI and the like, thromboxan A(TXA), thromboxan B(TXB) and the metabolites thereof, and in addition, the glycoprotein regulates not only one kind of PGs but also several kinds of PGs also in vitro. The activity of the glycoprotein in regulating the production of PGs and their metabolites is recognized by the following findings of the present inventors.

(i) The glycoprotein raised the level of cyclic adenosine monophosphate(c-AMP) which was closely related, as an intracellular messenger, to PGs (refer to Example 20).

(ii) As has been seen in the in vitro experiment on the metabolism of arachidonic acid taken into lymphocytes to some PGs (refer to Example 18), the glycoprotein participated the production of $PGD_2$, $PGE_2$, 6-keto-$PGF_{1\alpha}$ and $PGF_{2\alpha}$.

(iii) The glycoprotein affected in vitro the biosynthesis of PGE and $PGF_{2\alpha}$ in the cultured cancer cells (refer to Example 21).

(iv) As a result of administering the glycoprotein to cancer-bearing animals, the proliferation of the cancer was inhibited and the intra-cancer-cellular level of PGE was raised (refer to Example 22). In addition, the remarkably raised intraplasmic level of 6-keto-$PGF_{1\alpha}$ in cancer-bearing animal was reduced to the normal level by the administration of the glycoprotein.

(v) The anti-arrhythmic act of the glycoprotein was inhibited by indomethacin which inhibited the metabolism of prostaglandin (refer to Example 25).

In the case where the pharmaceutical composition according to the present invention is administered for the treatment of diabetes mellitus, rheumatism, ischemic heart diseases, ischemic cerebral diseases, hypertension, thrombosis, pains due to the accentuation of central nerve, pyrexia due to accentuation of central nerve, hyperlipemia, inflammatory diseases and nephrotic syndrome, and for regulating the production and metabolism of prostaglandins in a mammal, the pharmaceutical composition according to the present invention may be used as the followings.

The pharmaceutical composition according to the present invention can be administered in combination with the other pharmaceutical composition for reducing the level of blood pressure such as those containing the conventionally-used active ingredient such as a derivative of sulfonylurea without reducing the activity of the active ingredient of the conventional pharmaceutical composition.

The pharmaceutical composition according to the present invention can be used in combination with the other antirheumatic agents such as a formulation of gold, chloroquine, penicillamine and the like.

By the combined use of the pharmaceutical composition according to the present invention with a coronary dilator such as amyl nitrite and nitroglycerol, etc. in the case of fits, or another coronary dilator, in the non-fit case, such as a formulation of nitrite, a formulation of xantine, papaverin, dipyridamole, prenylamine, benziodalon, carbocromene, efloxate, 2,6-pyridine-dimethanol-bis(N-methylcarbamate), berapamil, nicotinic acid, etc., and a sedative such as phenobarbital, meprobamate, chlorodiazepoxide, reserpine, chloropromazine, etc., a combined effect is expectable. In addition, the pharmaceutical composition according to the present invention may be used in combination with an antiarteriosclerotic agent.

By the combined use of the pharmaceutical composition according to the present invention for ameliorating ischemic cerebral diseases with an agent for dilation of the cerebral blood vessels such as carbon dioxide, papaverine, buphenine, isoxsuprine, hexobendine, cyclandelate, ATP, ADP, adenosine phosphate, acetazolamide, pyritinol, raubasine, aqueous hypertonic solution of glucose, etc., a combined effect is expected. In addition, the pharmaceutical composition according to the present invention may be used in combination with an anti-arteriosclerotic agent.

In addition, the activity of the glycoprotein according to the present invention is not reduced even if the pharmaceutical composition according to the present invention is used in combination with a blocking agent broadly used as a hypotensive agent such as alkaloid, guanethidine, methyldopa and thiazide derivatives, and a combined effect is expectable.

Reinforcement of the effectiveness of the pharmaceutical composition according to the present invention is expectable by the combined use thereof with a conventional antithrombotic agent.

The combined use of the central nerve-repressing pharmaceutical composition according to the present invention with the other central nerve-repressing agent, for instance, a narcotic analgesic agent, a non-narcotic analgetic agent and an analgetic, anti-pyretic and anti-inflammatory agent such as those derived from salicylic acid, pyrazolone, indole, phenylacetic acid, anthranilic acid, thienopyridine, pyrimidine, pyrimidinylpyrazole, benzotriazine and benzothiazolinone exhibits the combined effect.

Since the active ingredient of the pharmaceutical composition according to the present invention shows an activity of reducing the levels of both cholesterol and $\beta$-lipoprotein in the blood and an activity of raising the level of LDL receptor, the pharmaceutical composition is useful as an antihyperlipemic pharmaceutical composition. Moreover, although the functional mechanism of the active ingredient of the pharmaceutical composition according to the present invention differs from those of the inhibitor of cholesterol-synthesis, the inhibitor of cholesterol-absorption and the eccritic of cholesterol which are now broadly used as the active ingredient respectively of the antihyperlipemic pharmaceutical composition, in the case where the glycoprotein according to the present invention is used in combination with each of the above-mentioned active ingredient of the other antihyperlipemic pharmaceutical compositions, the effect is higher than the sum of the effect of the active ingredient and the effect of the glycoprotein according to the present invention and accordingly, the combined use of the glycoprotein and the other active ingredient of each of the conventional antihyperlipemic pharmaceutical composition is an effective means for treating hyperlipemia.

The combined use of the glycoprotein according to the present invention with the other active ingredient of the conventional anti-inflammatory pharmaceutical composition, for instance, steroid formulations, non-steroid formulations and anti-inflammatory enzyme formulations exhibit a combined effect.

The glycoprotein according to the present invention may be used in combination with any other active ingredient of the conventional pharmaceutical compositions for ameliorating nephrotic syndrome, for instance, dexamethasone, betamethasone, prednisolone, indomethacin, dipyridamole and cyclophosphamide.

The administration of the pharmaceutical composition according to present invention may be carried out via one of several routes, and the glycoprotein according to the present invention may be used in combination with any one of the conventional prostaglandin-regulating pharmaceutical composition containing, as the active ingredient, aspirin, indomethacin, etc.

The glycoprotein according to the present invention may be administered orally or parenterally to human being, and preferably orally. Oral administration includes sublingual administration and parenteral administration includes subcutaneous injection, intramuscular injection, intravenous injection and instillation. The effective amount of administration of the glycoprotein depends on the species, the age, the individual difference and the morbid state of the object, however, in the cases of treating human patients, the daily dose rate is 10 to 1000 mg/kg preferably 20 to 600 mg/kg of the body weight, which is divided evenly into 1 to 3 portions so as to be administered one to three times per day.

For the case of oral administration, the pharmaceutical composition according to the present invention may take the solid form taken as it is such as tablet, granule, powder and capsule, the liquid form taken as it is such as solutions, suspensions, emulsions and syrups, mixtures taken after shaking or a solid form taken after dissolving in sterilized water not containing any pyretic substance. The pharmaceutical composition taken as a solid may contain the conventional additives such as binders, vehicles, lubricants, disintegrators, wettable agents, and the pharmaceutical composition taken as a liquid, may contain the conventionally used additives and preservatives. For the case of injection, the pharmaceutical composition may contain the other additives such as stabilizers, buffering agents, preservatives and isotonic agents and the product is supplied after filling in a dosage unit ampule or in a conventional container.

The present invention is explained in more detail in the following Examples; however, it should be recognized that the scope of the present invention is not restricted to these Examples.

EXAMPLE 1

Preparation of the glycoprotein of the present invention

Into 4 litres of an aqueous 0.1 N sodium hydroxide solution, 200 g of dried mycelia of *Coriolus versicolor* (Fr.) Quél. (FERM-P No. 2414(ATCC 20547)] of a moisture content of 8.8% and a gross nitrogen content of 2.5% were added, and the mycelia were extracted under agitation at a temperature of 90° to 95° C. for one hour, and then the mixture was cooled to below 50° C. and after adjusting the pH of the thus cooled mixture to 7.0 by aqueous 1N hydrochloric acid solution, the solid matter was removed from the mixture by suction filtration and the thus removed solid matter was washed with 500 ml of water. The mixture of the filtrate and the washings, amounting to 4.2 litres, was subjected to ultrafiltration by the use of a desk-top ultrafilter made by Amicon Inc. (provided with the ultrafiltration membrane: PM-5) under agitation and cooling under the operating pressure of 1.5 kg/cm$^2$ at 10° C., thereby removing low molecular weight substances of molecular weight of lower than 5,000, followed by concentration to obtain 300 ml of the processed aqueous extract. The aqueous extract was further subjected to freeze-drying to obtain about 26.6 g of a powdery substance liver brown in color in a yield of 13% of the mycelia. The thus obtained powdery substance had a moisture content of 7.5% and showed an elementary analytical composition of 40.5% of carbon, 6.2 of hydrogen, 5.8% of nitrogen and the balance of oxygen. The powdery substance was easily soluble in water.

The powdery substance showed an activity of inhibiting the proliferation of the transplanted sarcoma 180 as high as 90% when intraperitoneally injected to the transplanted mice and as high as 65% when orally administered to the transplanted mice.

EXAMPLE 2

Antidiabetic activity

Among a number of Wistar rat to which streptozocin had been intraperitoneally administered at a rate of 60 mg/kg, those in which glucosuria and positivity of blood sugar had been confirmed after about one week of the administration were administered with regular insulin. Among the thus treated animals, those once showed the reduction of the level of sugar both in urine and blood and in which high level of both glucosuria and blood sugar was confirmed after a few days of the administration of regular insulin were chosen as the model animals of diabetes mellitus for the following experiment:

After dissolving the glycoprotein of the present invention into distilled water, the aqueous solution was orally administered to each of the model animals at a dose rate of 30 or 300 mg/kg.

After 3, 6, 9 and 24 hours of the administration, blood specimen was taken from the caudal vein of each animal, and the content of glucose in the specimen was measured by enzymatic method while using RaBA kit, the results being shown in FIG. 1.

As are seen in FIG. 1, the administration of the glycoprotein of the present invention caused the reduction of glucose level in the blood of the thus treated rat, thereby verifying the effectiveness of the glycoprotein as a blood sugar-reducing agent.

In consideration of the above-mentioned toxicological property and the thus manifested pharmacological property of the glycoprotein of the present invention, it will be understood that the glycoprotein of the present invention can be put to practical use.

EXAMPLE 3

Anti-adjuvant arthritic activity

Among the rats to which a suspension of *Mycobacterium tuberculosis* in liquid paraffin had been injected subcutaneously into the pad of the right hind leg while following the method of Fujiwara et al. (1971), those showing the same extent of swelling of the hind leg after 14 days of the injection were chosen as the test animals and divided into two groups each consisting of 10 animals. To each animal of the first group, the glycoprotein of the present invention was orally administered at a daily dose rate of 1000 mg/kg every day for 7 days from the 15th day of injection. Then, the volume of the hind leg of each of the thus treated animals and that of each of the second group (not administered with the glycoprotein) were measured, and the antiarthritic activity of the glycoprotein was obtained by calculation according to the following formula:

$$\text{Antiarthritic activity (I.R.)(\%)} = (1 - T/C) \times 100$$

wherein:
T: means volume of the hind leg of the animal of the first group administered with the glycoprotein
C: means volume of the hind leg of the control animal of the second group to which the glycoprotein had not been administered.

As a result, the glycoprotein of the present invention showed a remarkable anti-adjuvant-arthritic activity of 35.9%.

EXAMPLE 4

Anti-chronic arthritic activity in a woman

To a woman of 62 in age who was suffering for 25 years from a disease diagnosed to be chronic arthritis of Classical, Stage of IV and Class 3, the glycoprotein of the present invention was administered every day for about 30 days at a daily dose of 3 g. As a result, the reduction of both the pain and the number of active joints of the patient was observed as will be seen in the following Table 2, and the patient's impression was highly improved to show the effectiveness of the glycoprotein of the present invention.

TABLE 2

| Item | Before administration | After administration for 30 days |
|---|---|---|
| Stiffness of joints felt in morning | 10 | 10 |
| Extent of pain | 1.5 | 0.5 |
| Grasping power | — | 82/100 (left/right) |
| Erythrocyte sedimentation value | 47 | 54 |
| CRT | ± | ± |
| Number of active joint | 4 | 1 |
| Impression of patient | — | very good |
| Judgement of the physician | — | improved |

EXAMPLE 5

Anti-chronic arthritic activity

As a result of the administration of the glycoprotein of the present invention at a daily dosage of 3 g for 6 months in combination with the administration of 6 tablets of Brufen ® and 2 tablets of Indacin suppository both of which had been administered to a woman of 47 in age suffering for 4 years from chronic arthritis diagnosed to be Classical, Stage of III and of Class 2, a remarkable effect of improvement was confirmed as follows:

| Item | Before administration | after 6 months' administration |
|---|---|---|
| Stiffness felt in morning | 60 | 0 |
| Extent of pain | 2 | 1 |
| Grasping power | 90/60 | 93/138 (left/right) |
| Number of active joint | 5 | 5 |
| Impression of patient | — | good |
| Judgement of the physician | — | improved |

EXAMPLE 6

Activity of increasing coronary blood flow

After preparing a cardiopulmonary specimen while using a group consisting of three normal beagles, an aqueous solution of the glycoprotein of the present invention prepared by dissolving the glycoprotein in a physiological saline was injected to the specimen from the upper large vein at a rate of 1, 10 and 100 mg/kg, respectively. The coronary blood flow was measured by an electromagnetic flowmeter inserted into the coronary sinus from the right atrium while using Morawity's cannula. The results are shown in Table 3. As are seen in Table 3, the average coronary blood flow showed an increase after the administration of the glycoprotein as compared to before the administration.

TABLE 3

| Activity of increasing the coronary blood flow | |
|---|---|
| Amount of Glycoprotein injected (mg/kg) | Rate of increase of blood as compared to the flow before injection (%) |
| 1 | 21.0 |
| 10 | 35.2 |
| 100 | 37.5 |

EXAMPLE 7

Activity of improving the capability of deformation of the erythrocyte

The glycoprotein of the present invention was administered to each of six groups of Wistar rats, each group being consisted of five animals, at the dose rate of 10–10,000 mg/kg, by oral and intraperitoneal administration, respectively. After 3 hours of the administration, blood was taken from each rat, and added to 10 times by weight of physiological saline. After stirring the mixture in a mixer, thereby mechanically hemolysing the erythrocytes inthe mixture, the mixture was subjected to centrifugal separation. The amount of hemoglobin ($A_i$) in the thus obtained supernatant liquid was measured by colorimetry. The same procedures were carried out except for using distilled water in stead of the physiological saline to obtain the amount of hemoglobin ($B_i$) in the supernatant liquid, and the extent of hemolysis ($H_i$) was calculated by the following formula:

$$H_i = \frac{A_i}{B_i} \times 100$$

The extent of hemolysis obtained from the blood of the control rat administered with distilled water instead of the glycoprotein of the present invention by the same procedures as above was calculated to be $H_c$.

Relative rate of hemolysis was calculated by the following formula while using the mean value of $H_i$ and $H_c$:

$$\text{Relative rate of hemolysis} = \frac{\text{mean value of } H_i}{\text{mean value of } H_c} \times 100$$

The thus obtained results are shown in Table 4 after classifying into the route of administration and the dose rate.

As are seen in Table 4, the reduction of the relative rate of hemolysis was observed in the administered groups regardless of the route of administration of the glycoprotein. Namely, administration of the glycoprotein of the present invention caused the improvement of the capability of the erythrocytes in deformation.

TABLE 4

| Activity of reducing the relative extent of hemolysis | | |
|---|---|---|
| Amount of glycoprotein administered (mg/kg) | Route of administration | Mean relative extent of hemolysis (%) |
| 10 | i.p. | 81 |
| 100 | i.p. | 74 |
| 1000 | i.p. | 72 |
| 0 (control) | i.p. | 100 |
| 100 | p.o. | 88 |
| 1000 | p.o. | 79 |
| 10000 | p.o. | 75 |
| 0 (control) | p.o. | 100 |

EXAMPLE 8

Activity of inhibiting the death due to thromboembolism

Following the method of Furlow et al, (refer to "Science" 187, 685, 1975), the glycoprotein was administered to each of ten rats of the two respective groups as follows:

First group: intraperitoneally at a dose rate of 100 mg/kg

Second group: orally at a dose rate of 1000 mg/kg

Control group: not administered with the glycoprotein

After 30 min of the administration, arachidonic acid was injected to each rat from the left carotid artery in the blood flow direction and the mortality of the rat was observed. The results are shown in Table 5.

TABLE 5

| Activity of inhibiting thromboembolic death | | |
|---|---|---|
| Dose rate (mg/kg) | Route of administration | Number of rats of a group Survived / Total |
| not administered | — | 0/10 |
| 100 | i.p. | 6/10 |
| 1000 | p.o. | 6/10 |

As are seen in Table 5, activity of the glycoprotein in inhibiting the death due to thromboembolism was recognized.

EXAMPLE 9

Hypotensive activity

Figure 2:
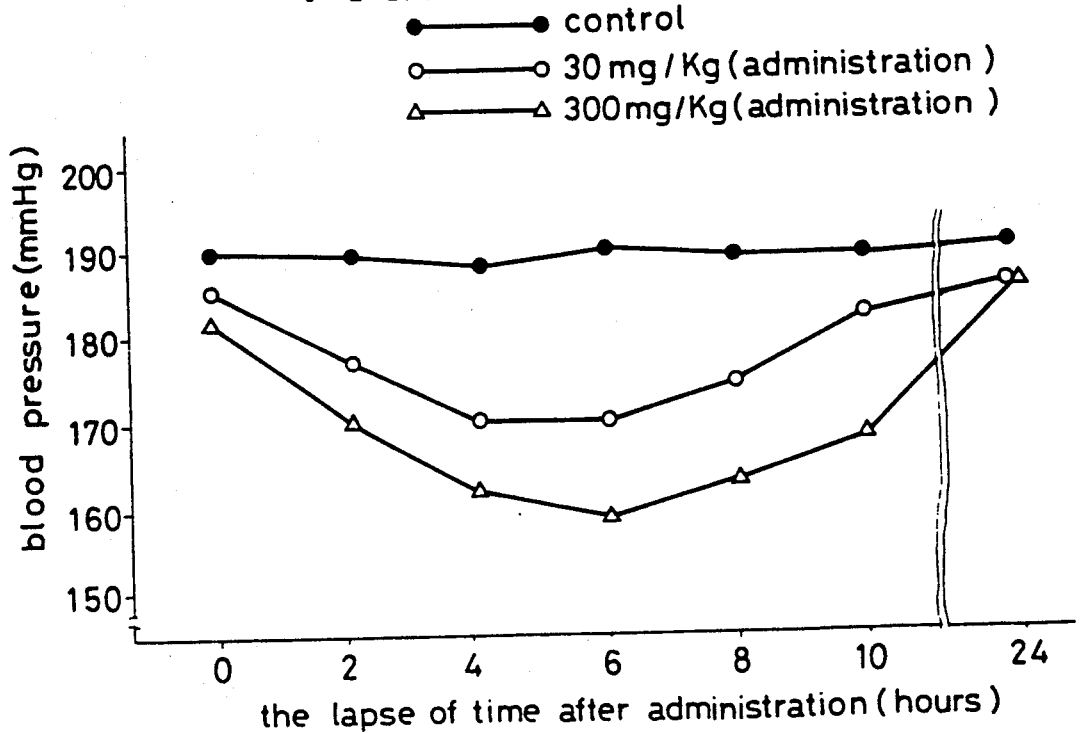
FIG. 2 is a chart showing the transition of the blood pressure of SHR (spontaneous hypertensive rats) after administration of the glycoprotein of the present invention.
Figure 3A:
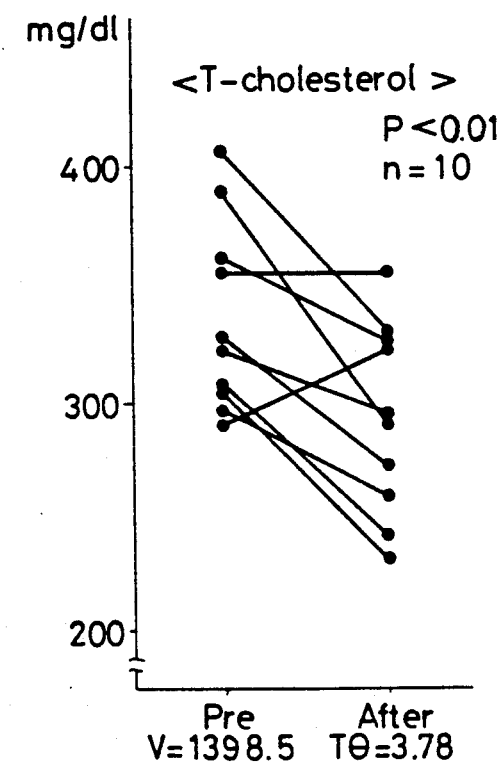
FIGS. 3 (a to d) shows the transition of each lipid in the blood of the patient of hyperlipemia to whom the glycoprotein according to the present invention was administered.
Figure 3B:
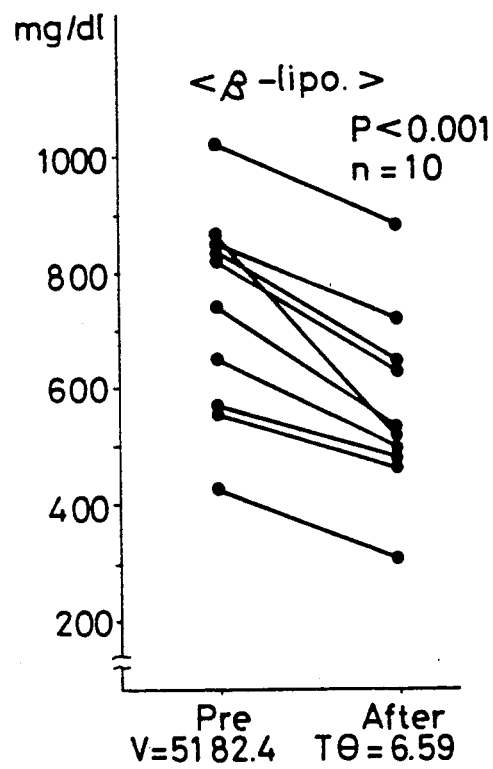
Figure 3C:
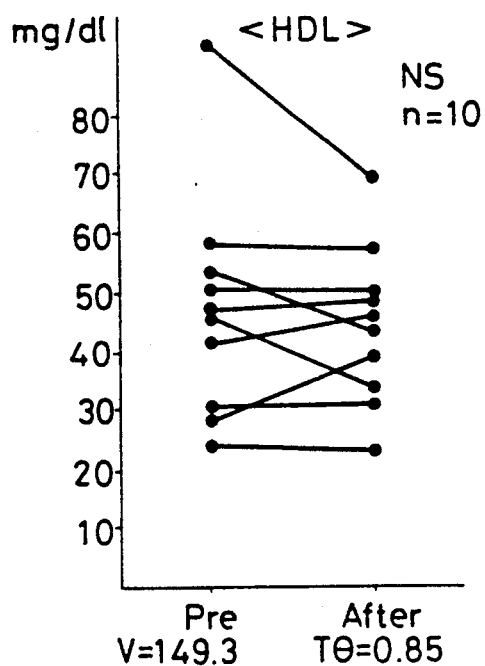
Figure 3D:
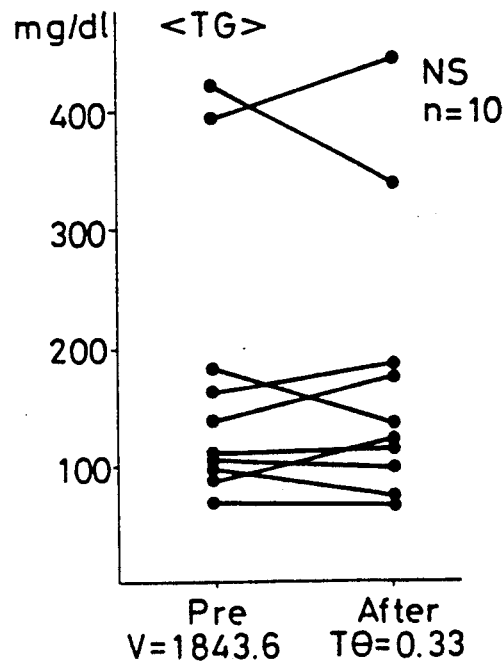

After dissolving the glycoprotein of the present invention in distilled water, the thus obtained aqueous solution was orally administered to each of rats of spontaneous hypertension, and the blood pressure of the thus treated rats was measured with the lapse of time, the results being shown in FIG. 2.

As are seen in FIG. 2, it is understandable that the hypotensive activity of the glycoprotein is excellent.

Because of the close correspondence between the spontaneous hypertension in rats and the human essential hypertension, the pharmaceutical composition containing the glycoprotein of the present invention can be said effective as a hypotensor.

EXAMPLE 10

Activity in inhibiting aggregation of platelets

Human venous blood was collected into an aqueous citrate solution (as an anticoagulant) at a weight ratio of 9:1, and after subjecting the mixture (of blood and the solution) to centrifugal separation for 6 min at 400 G, the supernatant fluid was collected. From the thus obtained supernatant fluid, a platelet rich plasma (hereinafter referred to PRP) was prepared, and the residue of centrifugation was further subjected to centrifugal separation for 20 min at 700 G to obtain a supernatant fluid (hereinafter referred to the platelet poor plasma (hereinafter referred to as PPP).

(1) The case where the glycoprotein is not added

Each of the three coagulants, arachidonic acid at the concentration of 1.64 mM, collagen at the concentration of 0.26 mg/ml and adenosine-diphosphoric acid (ADP) at the concentration of 50 micro M was added to PRP, and transmissivity of aggregation, which was indicated by difference of transmission between PRP and PPP was measured by an agligometer (made by Biodata Co., model PAP-3). The value corresponds to the extent of aggregation of platelets by each of the coagulants, and was referred to $A_{1i}$.

(2) The case where the glycoprotein is added

The glycoprotein of the present invention was added to PRP and PPP, respectively at a rate of 1 mg/ml thereof, and after 2 min of the addition, each of the three coagulants was added to the thus treated PRP, and platelets aggregation were measured. In this case (2), the value corresponds to the extent of aggregation of platelets by each of the coagulants in the presence of the glycoprotein, and was referred to $A_{2i}$.

The rate of inhibiting aggregation of platelets due to each of the coagulants by the glycoprotein (I.R. %) was obtained by the formula:

$$I.R.(\%) = \frac{A_{1i} - A_{2i}}{A_{1i}} \times 100$$

The results are shown in Table 6:

TABLE 6

| Specimen | Rate of inhibiting aggregation (%) due to | | |
|---|---|---|---|
| | ADP | Collagen | Arachidonic acid |
| Platelets added with the glycoprotein | 77 | 76 | 78 |
| Control (platelets without adding the glycoprotein) | — | — | — |

As are seen in Table 6, the glycoprotein of the present invention showed the activity of inhibiting aggregation due to any one of the coagulants.

EXAMPLE 11

Inhibition of the death due to thromboembolism

The glycoprotein of the present invention was orally administered at a dose rate of 1 g/kg to each of the ten male ddY mice of body weight of 20 to 22 g, and after 3 hours of the administration, ADP at a rate of 400 mg/kg or soluble collagen (made by Sigma Co.) at a rate of 0.2 ml/kg was intravenously administered to each of the mice. Thereafter, the mortality of the group of mice was observed after 10 min of the administration of the coagulant. To each of the other ten male ddY mice, distilled water was orally administered instead of the glycoprotein according to the present invention while using them as control. The results are shown in Table 7.

As shown in Table 7, the glycoprotein of the present invention showed the activity of inhibiting the death due to thromboembolism by the coagulant.

TABLE 7

| Group of mice | Number of dead animal/ total number of animal | |
|---|---|---|
| | ADP | Collagen |
| Those administered with glycoprotein | 4/10 | 4/10 |
| Control | 10/10 | 10/10 |

EXAMPLE 12

(1-1) Analgetic activity

Examination of analgetic activity by mechanical stimulation

Experimental animals were selected from female ICR mice by applying a pressure to the caudal base point while using a pressure stimulating apparatus of Takagi and Kameyama (made by Natsume Works.) and choosing the individuals showing the threshold value of pseudo-escaping in a range of 50 to 80 mmHg in pressure.

After dividing the thus selected animals into groups each consisting of 10 animals, the glycoprotein of the present invention was administered each animal of the first group orally at a dose rate of 1000 mg/kg and subjected to the apparatus. Thus, the pressure at the time when the animal showed a pseudo-escaping reaction and the time (sec) until the animal showed the pseudo-escaping reaction were determined, the pressure and the time being used for judging the analgetic effect. The results are shown in Table 8.

TABLE 8

| Group | Pressure (mmHg) at the time when: | Time (sec) until: |
|---|---|---|
| | pseudo-escaping reaction was shown (average) | |
| Administered with the glycoprotein | 75 | 35 |
| Not administered with glycoprotein (control) | 60 | 28 |

As are shown in Table 8, every animal administered with the glycoprotein of the present invention showed a higher value of the pressure and a longer time than control, thus confirming the analgetic activity of the glycoprotein of the present invention.

Examination of analgetic activity by chemical stimulation

After dividing 20 female ICR mice of 5 to 6 weeks after birth were divided in two groups each consisting of 10 animals, the glycoprotein of the present invention was orally administered to each of the mice of the first group at a dose rate of 1000 mg/kg, and after 30 min of the administration, an aqueous 0.6% solution of acetic acid was intraperitoneally injected into each of the thus treated mice. The number of writhing caused by the injection was counted by Kostet et al. method (1959) within 10 min after 10 min of the injection, and the rate of suppressing the writhing (%) due to the glycoprotein was calculated by the following formula:

Rate of suppressing (%) = $(1 - T/C) \times 100$ wherein

T is the average number of writhing of the treated group

C is the average number of writhing of the group not administered with the glycoprotein.

The rate of suppressing the writhing by the glycoprotein was 52.1%, namely, the number of writhing being clearly reduced as compared to that in control. In other words, the glycoprotein of the present invention showed a significant analgetic activity.

(1-2) Antipyretic activity

Following the method of Winter et al. (1961), an aqueous 20% suspension of beer yeast was subcutaneously injected into each of six rats of a group, and after fasting the animals for 10 hours, the glycoprotein of the present invention was orally administered to each of the thus treated rats at a dose rate of 1000 mg/kg. Thereafter, the rectal temperature of each of the animals was measured with the lapse of time, thereby examining the antipyretic activity of the glycoprotein. The results are shown in Table 9 with the results on the control animals injected, however, not administered with the glycoprotein.

TABLE 9

| Group | Rectal temperature (average) after 2 hours of administration Rectal temperature (average) (°C.) |
|---|---|
| Not injected and not administered | 37.0 |
| Injected but not administered | 38.5 |
| Injected and administered | 37.5 |

As are seen in Table 9, the glycoprotein of the present invention showed an antipyretic activity. Namely, the temperature of the rats injected beer yeast and administered with the glycoprotein was kept at the level almost as the same as that of the rats not injected nor administered.

EXAMPLE 13

(1-1) Activity of reducing the level of lipids in the blood of the patients suffering from hyperlipemia The glycoprotein of the present invention (hereinafter referred to as the glycoprotein) was orally administered continuously for about one month at a daily dosage of 3 g to 10 patients (3 men and 7 women) suffering from hyperlipemia. The levels of T-cholesterol, $\beta$-lipoprotein, high density lipoprotein (HDL), triglycerides (TG) before the administration were 293 to 405 mg/dl (mean 340 mg/dl), 418 to 1038 mg/dl (mean 741 mg/dl), 26.2 to 96.5 mg/dl (mean 49 mg/dl) and 73 to 425 mg/dl (mean 181 mg/dl), respectively in the blood of the patients. Although these patients had been administered with various anti-hyperlipemic pharmaceutical composition for at least 4 months, they were suffering from hyperlipemia, namely the cases to which the conventional anti-hyperlipemic pharmaceutical composition was ineffective.

Blood specimen was taken from each of the patients before beginning the administration of the glycoprotein of the present invention and during the administration two times, 14th and 28th day from the day of beginning the administration, and the lipid therein was examined, the results on the blood specimen taken on 28th day being shown in FIG. 3 (a to d). As are seen in FIG. 3, although the glycoprotein showed no effect on the values of HDL and TG, the levels of $\beta$-lipoprotein and T-cholesterol were significantly reduced. Particularly, the level of $\beta$-lipoprotein was reduced in all cases by 150 mg/dl in the average, the mean rate of reduction being 20%.

(1-2) Activity of ameliorating LDL-receptor in human fibroblast

Fibroblasts of a patient suffering from a hereditary disease, heterotype familiar hyperlipemia $II_a$ characterized by the hyperplasia of Achilles's tendon were used as an experimental material, and were subjected to subculture in MEM containing 20% fetal bovine serum following the modified method of Goldstein et al, fifth to tenth generation being handled.

Figure 4:
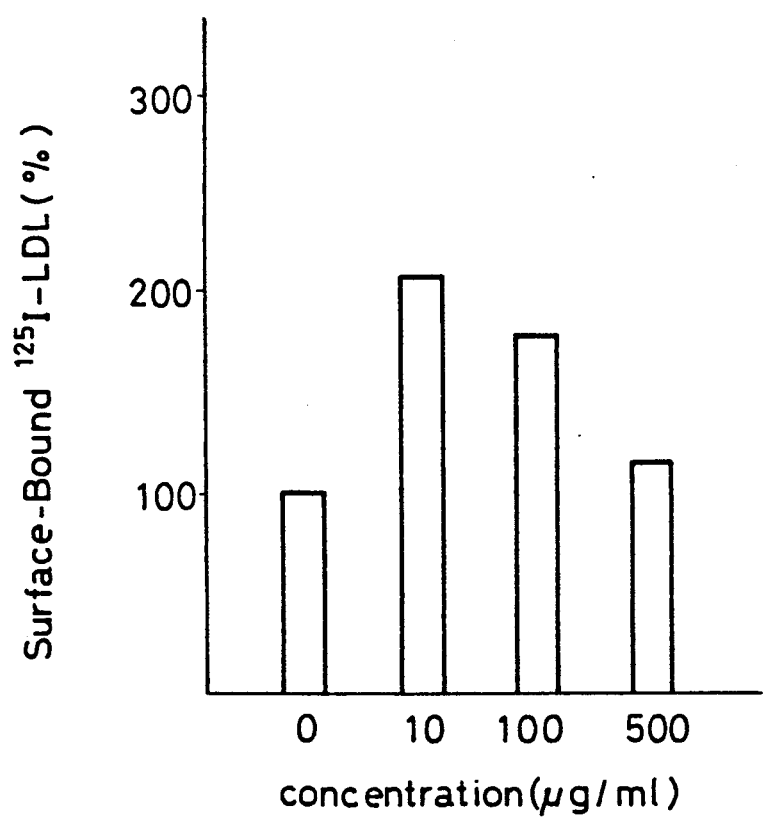
FIG. 4 is a graph showing the influence of the glycoprotein according to the present invention on the LDL-receptor of human fibroblasts.

After culturing the fibroblasts in a dish of 6 cm in diameter until they proliferated to a predetermined amount, 5% lipoprotein deficient serum and the glycoprotein at a concentration shown in FIG. 4 were added to the dish, and after further culturing for 48 hours, $I^{125}$-labelled LDL was added to the dish, and after further culturing for 6 hours, the cells adhering to the dish were washed 6 times with phosphate buffer solution and cultured in a HEPES buffer solution added with sodium dextran sulfate for one hour.

The radioactivity of the liquid of the thus cultured fibroblasts was determined as the amount of the surface-binding LDL, i.e., the number of the receptor ($N_i$).

The same fibroblasts were cultured in the same manner as above except for adding the glycoprotein of the present invention, and the radioactivity of the liquid of the thus cultured fibroblasts was determined as above, the number of the receptor being $N_O$.

The activity of raising the number of the surface bound $I^{125}$-labelled LDL was represented by $(N_i/N_O) \times 100$ (%), and is shown in FIG. 4.

As are seen in FIG. 4, the surface-bound $I^{125}$-LDL was increased by the addition of the glycoprotein, and it shows the increase of LDL-receptor.

EXAMPLE 14

(1-1) Activity of repressing edema due to carragheenin

Following the method of Van Armen et al. (1963), after one hour of forcible oral administration of the glycoprotein of the present invention to each of ten rats of the first group at a dose rate of 1000 mg/kg, an aqueous suspension of 1% carragheenin in a physiological saline was injected into the footpad of the right hind leg of the rat at a rate of 0.1 ml/animal. Thereafter, the volume of the right hind leg was determined with the lapse of time, and the rate of repressing the swelling of the leg (due to edema by carragheenin) was calculated according to the following formula:

Rate of repressing (%) = $(1 - T/C) \times 100$ wherein
T is the volume (average) of the right hind leg of the rat administered with the glycoprotein and injected with carragheenin, and
C is that of the rat not administered with the glycoprotein and injected with carragheenin.

As a result, the glycoprotein showed a rate of repressing edema due to carragheenin as high as 50.6%, and it was found that the glycoprotein has an excellent anti-inflammatory activity.

(1-2) Activity of repressing granuloma

Following the method of Winter et al. (1963), two cotton wool pellets each weighing $30 \pm 1$ mg were implanted subcutaneously into the back of each of 6 rats of the first group in the symmetrical positions to the median line, and the thus treated animals were administered orally with the glycoprotein of the present invention continuously for 7 days at a daily dosage of 1000 mg/kg. On the day after the last day of administration, the granuloma on the back of the rat was extirpated, dried and weighed.

The activity of the glycoprotein in repressing the granuloma was obtained by the same procedures as in (1-1).

As a result, the weight of the granuloma of every rat administered with the glycoprotein was smaller than that of every rat not administered with the glycoprotein. Namely, the glycoprotein of the present invention showed a average rate of repressing the granuloma due to cotton wool pellet of 49.9%.

(1-3) Activity of repressing exudation

Following the method of Baris et al. (1965), air was injected subcutaneously into the back of each of 6 rats of a group to form a pouch therein, and 0.5 ml of a 1% solution of croton oil in sesame oil was injected into the thus formed pouch. Thereafter, the glycoprotein as administered to the thus treated rats continuously for 5 days at a daily dosage of 1000 mg/kg. On the day after the last day of the administration, the volume of liquid exuded into the pouch was determined.

The rate of repressing the exudation was calculated as in (1-1). Namely, the glycoprotein of the present invention showed the average rate of repressing the exudation of 39.7%, the result showing the activity of the glycoprotein in repressing the exudation.

(1-4) Activity of repressing the aduvant-arthritis due to bacteria

Following the method of Fujiwara et al. (1971), a suspension of *Mycobacterium tuberculosis* in liquid paraffin was subcutaneously injected into the footpad of the right hind leg of each of a number of rats, and on the 14th day of the injection, twenty rats with the same volume of the right hind leg were selected from the thus treated rats. After dividing the thus chosen rats into two groups each consisting of 10 animals, the glycoprotein of the present invention was orally administered continuously for 7 days at a daily dose rate of 1000 mg/kg. Thereafter, the volume of the right hind leg of each of the thus treated ten animals, and that of the animals injected but not administered were determined to obtain the rate of repressing the swelling of the right hind leg due to adjuvant arthritis.

The glycoprotein showed the activity of repressing the occurrence of adjuvant arthritis of 35.9%.

EXAMPLE 15

Activity of ameliorating a nephrose-like morbid state

After preparing two groups of Donryu rats each weighing about 200 g, a group consisting of 5 animals, the glycoprotein of the present invention was administered to each of the rats in the first group continuously for 5 days at an oral, daily dose rate of 500 mg/kg and then aminonucleoside (hereinafter referred to AN) was subcutaneously injected as a solution in a physiological saline once a day for continuous 6 days at a daily dose rate of 15 mg/kg. AN has been known to cause proteinuria. To each of the rats of the second group, the glycoprotein was not administered but AN was administered in the same manner as in the first group.

Thereafter, the urine was collected every day from the thus treated rats of the two groups to examine the content of nitrogen in the urine specimens by Kjeldahl method, which was calculated to the content of protein therein.

Figure 5:
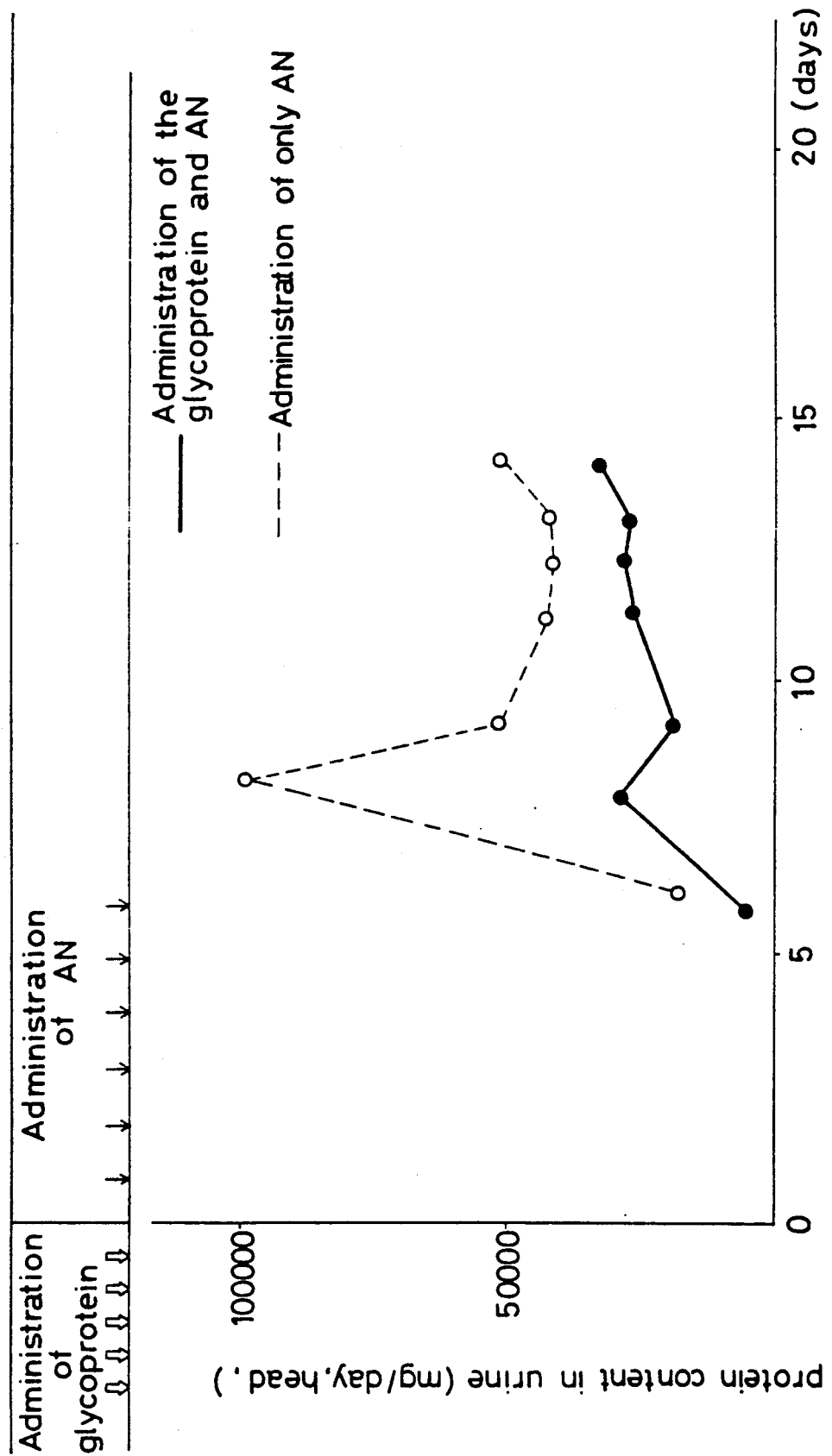
FIG. 5 shows the transition of the amount of protein in the daily urine of the Donryu rat which had been made to show nephrosis-like symptoms by the administration of AN with the lapse of time, and also the transition of the amount of protein in the daily urine of the Donryu rat which had been administered preliminarily with the glycoprotein of the present invention and then AN was administered with the lapse of time.

The results are shown in FIG. 5. As will be seen in FIG. 5, the preliminary administration of the glycoprotein could repress the occurrence of proteinuria due to AN.

EXAMPLE 16

A case of treatment of lupus nephrosis

Figure 6:
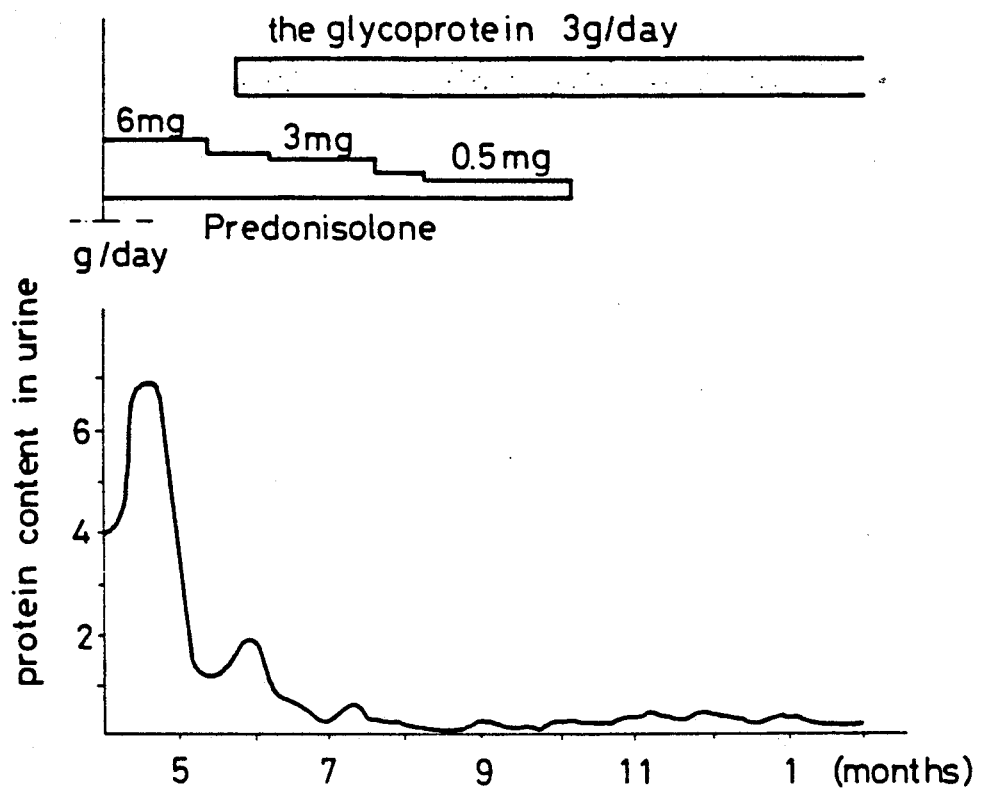
FIG. 6 shows the transition of the amount of protein in the urine of a patient of lupus nephritis before and during the administration of the glycoprotein according to the present invention to the patient, with the lapse of time.

To a woman of 35 in age diagnosed to be lupus nephrosis, the glycoprotein of the present invention was orally administered continuously for more than one month at a daily dosage of 3 g in combination with the oral administration of prednisolone at a daily dosage shown in FIG. 6 for 10 days.

Her urine was daily collected to be analyzed for nitrogen therein, the value being transformed into the amount of protein in the daily urine. The results are shown in FIG. 6. As will be seen in FIG. 6, it was shown that the glycoprotein is active in ameliorating lupus nephrosis.

EXAMPLE 17

A case of treatment of diabetic nephropathy

Figure 7:
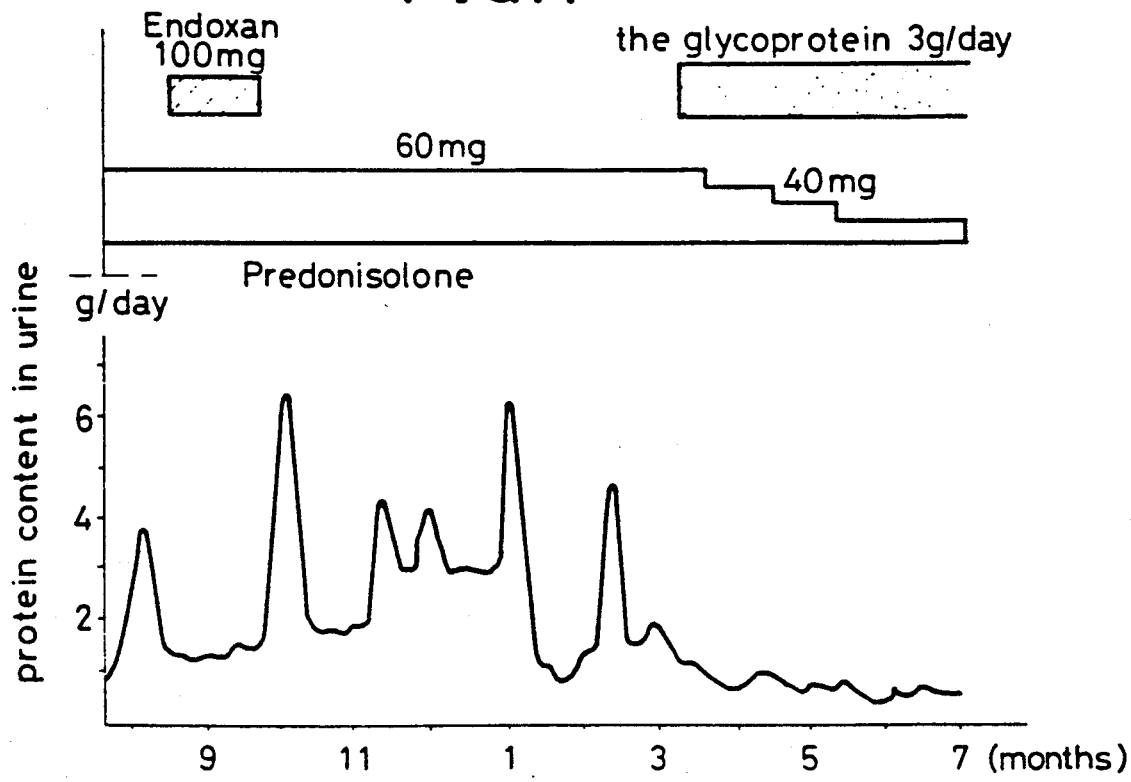
FIG. 7 shows the transition of the amount of protein in the urine of the patient of diabetic nephropathy with the lapse of time before and during the administration of the glycoprotein of the present invention.

To a woman of 45 in age diagnosed to be diabetic nephropathy, prednisolone and Endoxan ® were orally administered as are shown in FIG. 7 and from the time shown in FIG. 7, the oral administration of the glycoprotein of the present invention was started at a daily dose of 3 g. Her urine wad daily collected to be analyzed for nitrogen therein, the data being calculated to the amount of protein in the urine and shown also in FIG. 7.

As will be seen in FIG. 7, it was shown that the glycoprotein of the present invention is effective in ameliorating diabetic nephropathy.

EXAMPLE 18

Effect of the glycoprotein on the metabolism of arachidonic acid (which has been taken into lymphocytes) into PGs in the lymphocyte The lymphocytes were taken out from the spleen of a BALB/c mouse, and after suspending the lymphocytes in Eagle's MEM culture medium at a rate of $10^7$ cells/ml, 2 μCi of $^3$H-labelled arachidonic acid was added to the aqueous suspension and the mixture was incubated for 90 min at 37° C. After washing the thus incubated matter 3 times with Eagle's MEM culture medium, the cells were again brought into suspension in Eagle's MEM culture medium at a rate of $10^7$ cells/ml. Thus prepared suspension was equally poured into six siliconed test tubes by 2 ml/test tube.

Into the first two test tubes, the glycoprotein of the present invention was added at a rate of 10 μg/ml, and into the second two tubes, the glycoprotein was added at a rate of 100 μg/ml and the third two tubes were used as control without adding the glycoprotein.

After incubating the thus prepared six test tubes for 60 min at 37° C., the test tubes were subjected to centrifugation for 5 min at 0° C. under 1200 r.p.m., and the thus obtained pellets of cultured cells from each two test tubes were put into a mixture of 2 ml of Eagle's MEM culture medium and 5 ml of petroleum ether, and after shaking the mixture and removing the petroleum ether layer, the thus remaining aqueous layer was adjusted to pH of 3.5 by addition of aqueous 0.5N hydrochloric acid solution.

The thus obtained acidic liquid was extracted 3 times with each 5 ml of ether, and after evaporating ether off from the ether extract, the dried solid was subjected to esterification by a diazomethane solution. The product of esterification was fractioned by thin layer chromatography while developing with a 90:50:20:100 by volume mixture of ethyl acetate, isooctane, acetic acid and water to obtained fractioned spots which were identified by the authentic specimens of $PGD_2$, $PGE_2$, $PGF_{2\alpha}$ and 6-keto-$PGF_{1\alpha}$.

Each of the thus obtained, fractioned points was taken together with silica gel layer of the chromatographic column at the point and suspended in a liquid scintillation liquid, and then applied to a scintillation counter to obtain the count number due to $^3$H bound to each of PGs, thereby obtaining the amount of each of PGs.

As a result, it was found that the amount of $PGD_2$ and the amount of $PGE_2$ formed in the two tubes containing 10 μg, and in the two tubes containing 100 μg of the glycoprotein were remarkably larger than those in the two tubes not containing the glycoprotein. The amount of $PGF_{2\alpha}$ and the amount of 6-keto-$PGF_{1\alpha}$ in the former were also larger than those in the latter, however, the difference between the groups was not so remarkable as in the former.

EXAMPLE 19

Effect of the glycoprotein on the production of PGs in the jejunum eviscerated from a rabbit Pieces of the jejunum eviscerated from a female Japanese rabbit of about 2 kg in body weight were incubated in a Krebs' bicarbonate liquid placed in a reflux-incubator for 30 min under a flow of a 95:5 by volume mixture of gaseous oxygen and gaseous carbon dioxide at 37° C., and the amount of PGE present in the liquid culture medium was determined.

The same experiment was carried out, however, on the pieces of the jejunum eviscerated from another female Japanese rabbit to which the glycoprotein had been orally administered at a dose rate of 1 g/kg 2 hours before the operation.

It was found, as a result, that the amount of PGE was larger in the incubated liquid culture medium of the jejunum taken from the rabbit to which the glycoprotein had been administered than that in the first experiment on the rabbit not administered with the glycoprotein.

EXAMPLE 20

Effect of the glycoprotein on the level of c-AMP in the tumour cells of sarcoma 180

A mixture of $10^7$ cells of the ascitogenous tumour taken from the abdomen of a sarcoma 180 cancer-bearing mouse, Eagle's MEM culture medium and the glycoprotein of the present invention in an amount of 100 g/ml of the Eagle's MEM culture medium was cultured for 5 min at room temperature. After ending the culture, the thus cultured medium containing the cells was boiled, homogenized and subjected to centrifugal separation. The level of c-AMP in the thus obtained supernatant liquid was determined by the method of Gilman.

The same procedures as above were carried out while without adding the glycoprotein of the present invention to find the level of c-AMP in the supernatant liquid as control.

As a result, the level of c-AMP in the case of adding the glycoprotein was 118 pmol/$10^8$ cells and on the other hand, the level of c-AMP in the case of not adding the glycoprotein was 89 pmol/$10^8$ cells.

The result shows that the glycoprotein of the present invention has an activity of raising the level of c-AMP in the tumour cells of sarcoma 180 ascitogenous tumour.

EXAMPLE 21

Effect of the glycoprotein on PGE and $PGF_{2\alpha}$ in the cultured cancer cells Into 10 ml of the culture medium prepared by adding 10% by volume of bovine fetal serum to Eagle's MEM culture medium, the glycoprotein of the present invention was added at a rate of 50 μg/ml, and after placing the thus prepared culture medium in a flask for tissue culture of 75 cm 2 in the base area (Code No. 25110, made by Corning Co. U.S.A), $5 \times 10^5$ cells of mononuclear cultured cell of human leukemia (Strain J-111) were inoculated, and cultured for 7 days at 37° C. under a flow of 95:5 by volume mixture of air and carbon dioxide, the culture medium having been exchanged with the new one on the 2nd and 4th day of culture.

After the culture was over, the finished culture medium was subjected to centrifugal separation at 4° C. under 1500 r.p.m. to obtain a supernatant liquid.

The respective contents of PGE and $PGF_{2\alpha}$ in the thus obtained supernatant liquid were determined by the $^3$H-Prostaglandin E radioimmunoassay kit and the $^3$H-prostaglandin F radioimmunoassay kit (both kits made by Clinical Assay Co., U.S.A), respectively.

Figure 8:
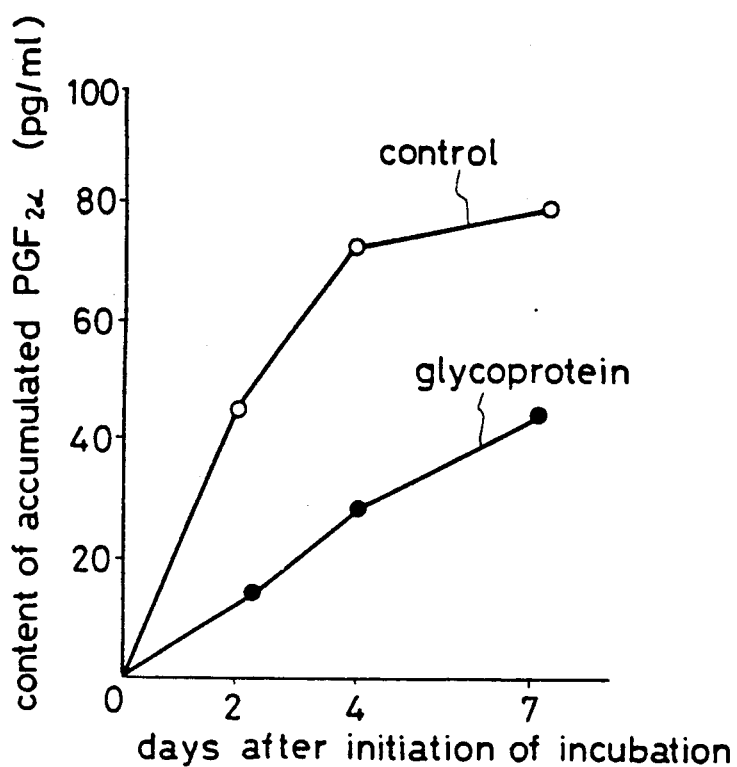
FIGS. 8 and 9 are the diagrams showing the activity of the glycoprotein of the present invention in regulating PGE and $PGF_{2\alpha}$ in the cultured media as the results of experiments in Example 21.
Figure 9:
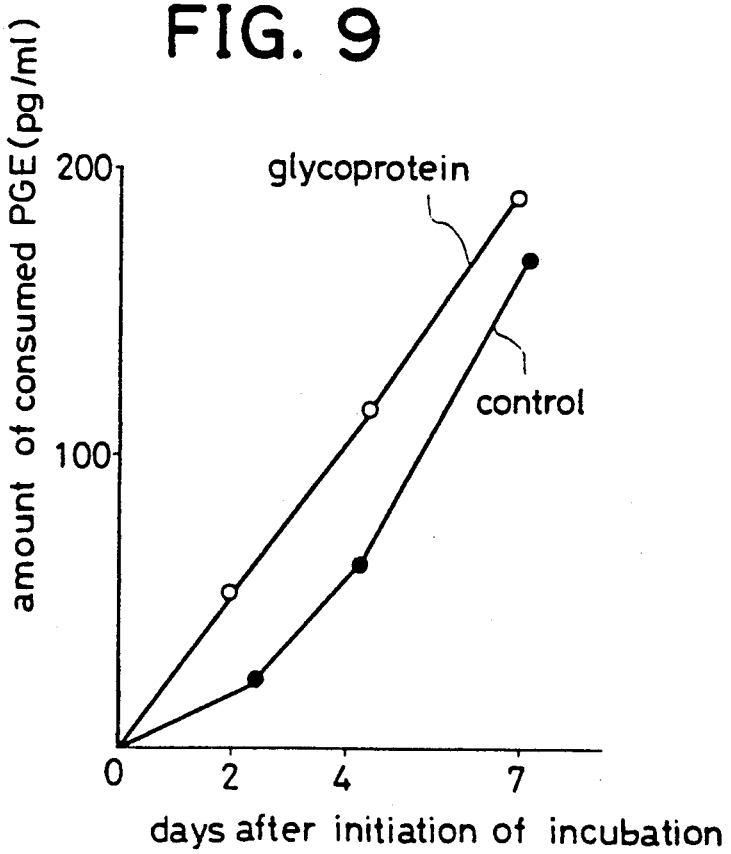

By comparing the thus obtained levels of the PGs to the levels obtained in the same experiment as above except for not adding the glycoprotein of the present invention, it was found, as are seen in FIGS. 8 and 9, that the addition of the glycoprotein in the culture medium caused the reduction of the levels of PGE and $PGF_{2\alpha}$ in the finished culture medium.

EXAMPLE 22

Effect of the glycoprotein on the level of PGE in the cells of Ehrlich cancer

To each of female C57BL/6 mice in 8th week after birth, the cells of Ehrlich cancer were subcutaneously transplanted at a rate of $10^6$ cells per animal, and after dividing the thus treated mice evenly into two groups, the glycoprotein of the present invention was orally administered every day from the second day of transplantation to each of the mice of the first group at a daily dose rate of 1 g/kg for 14 days without administering to the mice of the second group.

After 2 weeks of transplantation, all the mice were sacrificed by ether, and the tumours therein were eviscerated.

The tumour tissue obtained from each group of the mice were cut into minute pieces by scissors, and after placing the pieces in a glass-homogenizer, methanol was added at a rate of 7 ml per 1 g of the tumour tissue, and the mixture was homogenized at 0° C. After filtering the homogenate by a sheet of filter paper, the thus obtained filtrate was mixed well with 2 times by volume of chloroform, and the mixture was left to stand for 30 min at 4° C.

After removing the precipitated proteins in the mixture by filtration, the filtrate was dried to solid by a rotary evaporator, and after mixing the dried material with 2 ml of a mixture of chloroform, methanol and an aqueous diluted hydrochloric acid solution of pH of 2.0 in a separatory funnel to obtain a solution in which the dried material dissolved. Thereafter, the content of PGE in the thus obtained solution was determined by the $^3$H-Prostaglandin E radioimmunoassay kit (refer to Example 21).

As a result, the content of PGE in the solution obtained from the mice to which the glycoprotein of the present invention had been administered was 4.7 ng/g tumour, and on the other hand, the content of PGE in the solution obtained from the mice not administered with the glycoprotein was 1.8 ng/g tumour.

Namely, the glycoprotein showed an activity of raising the level of PGE in the tumour cells.

EXAMPLE 23

Effect of the glycoprotein in preventing metastasis of transplanted cancer cells to the lung of mouse Thirty female C3H/He mice in 8th week after birth were divided evenly into 3 groups, and after orally administering the glycoprotein of the present invention three times, namely 13, 7 and 1 hour before the undermentioned transplantation to each mouse of the first group, the MH 134 hepatoma cells were at a rate of $2 \times 10^6$ cells/animal from the caudal vein of each of all the mice, and after 5, 11 and 17 hours of the transplantation, the glycoprotein of the present invention was orally administered to each mouse of the second group in the rate of 1 g/kg of body weight, those mice of the third group being not administered with the glycoprotein.

After two weeks of the transplantation, all the mice were sacrificed and the respective lungs were eviscerated, and the number of the cancerous lesion due to metastasis of the transplanted hepatoma cells and the number of the mice having metastatic lesion(s) were counted to find the rate of positivity of metastasis by calculating according to the following formula:

Rate of positivity of metastasis $= (P/T) \times 100$ wherein

P is the number of mice having metastatic lesion(s) and

T is the total number of mice in the group $= 10$

As a result, in the first and second groups, the rate of positivity of metastasis was 60% and the average number of the metastatic lesion(s) was 2.1/animal, and in the third group, the positivity of metastasis was 100% and the average number of the metastatic lesion(s) was 4.5/animal.

Namely, the effectiveness of oral administration of the glycoprotein of the present invention in preventing the metastasis of transplanted cancer cells was confirmed.

EXAMPLE 24

Effect of the glycoprotein in regulating the level of 6-keto-PGF$_{1\alpha}$ in the blood of spontaneous hypertensive rats to which sarcomatous cells were transplanted To each of the rats suffering from spontaneous hypertension, $10^6$ cells of the sarcoma induced by methylcholanthrene were subcutaneously transplanted in the back thereof, and the rats were evenly divided into two groups. To the rats of the first group, the glycoprotein of the present invention was orally administered every day for 13 days from after 24 hours of the transplantation at a daily dose rate of 1000 mg/kg while not administering thereof to the rats of the second group.

After two weeks of the transplantation, blood specimen was collected from the vena cava inferior of every one of the tumour-cell-transplanted rats.

The plasma of each blood specimen was extracted with ether, and after obtaining the lipid fraction by subjecting the plasma to thin layer chromatography, the lipid fraction was converted into a methyloxim-silyl derivative. The derivative was subjected to gas-chromatography and mass-spectrography to find the amount of 6-keto-PGF$_{1\alpha}$ in the plasma.

As a result, the amount of 6-keto-PGF$_{1\alpha}$ in the plasma of the rat transplanted with the sarcomatous cells and administered with the glycoprotein was on the average 4.4 ng/ml plasma and on the other hand, that in the plasma of the rat transplanted with the sarcomatous cells and not administered with the glycoprotein was on the average 11.0 ng/ml of plasma. For reference, that of the plasma of the rat not transplanted nor administered was 3.0 ng/ml of plasma.

Namely, the orally administered glycoprotein of the present invention showed an activity of maintaining the plasmic level of 6-keto-PGF$_{1\alpha}$ of the rat transplanted with the methyl-cholanthrene-induced sarcomatous cells nearly at the same as that of the normal and intact rats.

EXAMPLE 25

Anti-arrhythmic activity of the glycoprotein

Female Wistar rats of about 200 g in body weight were evenly divided into four groups, and each rat of the first group was subjected to intravenous injection of an arrhythmia-inducing agent, aconitine, at 50 g/kg under anesthesia by urethane to cause the arrhythmic state in the rat. To each rat of the second group, the glycoprotein of the present invention was orally administered at a dose rate of 1000 mg/kg and after one hour of the administration, the same injection of aconitine was carried out. By comparing the electrocardiogram of the rat of the first group with that of the rat of the second group, it was found that the administered glycoprotein acted to improve the arrhythmic state.

In the next experiment, to each rat of the third and fourth groups, the same oral administration of the glycoprotein was carried out as in the second group, and then, indomethacin which is an inhibitor of metabolism of prostaglandins was administered intravenously in the rate of 10 mg/kg, resulting in disappearing of anti-arrhythmic activity of the glycoprotein according to the present invention.

Accordingly, the anti-arrhythmic effect of the glycoprotein according to the present invention is induced through prostaglandins.

EXAMPLE 26

Formulation of a pharmaceutical composition

Capsules each containing 330 mg of the glycoprotein of the present invention were prepared by filling the hard capsules #0 with the glycoprotein as it is while using an automatic filler under a pressure.

What is claimed is:

1. A method for increasing or decreasing the production or metabolism of prostaglandins in a human, which comprises:
administering to a human in need thereof a prostaglandin increasing or decreasing effective amount of glycoprotein having a molecular weight of 5000 to 300,000, as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

2. The method of claim 1, wherein said fungal species of the genus Coriolus is the strand *Coriolus versicolor* (Fr.) Quél. identified by ATCC No. 20547.

3. A method for the treatment of diabetes mellitus, which comprises:
administering to a human suffering from diabetes mellitus a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

4. A method for the treatment of rheumatism, which comprises:
administering to a human suffering from rheumatism a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

5. A method for the treatment of ischemic heart diseases which comprises:
administering to a human suffering from ischemic heart diseases a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

6. A method for the treatment of ischemic cerebral diseases which comprises:
administering to a human suffering from ischemic cerebral diseases a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

7. A method for the treatment of hypertension, which comprises:
administering to a human suffering from hypertension a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

8. A method for the treatment of thrombosis, which comprises:
administering to a human suffering from thrombosis a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

9. A method for the treatment of pains due to the accentuation of the central nerve, which comprises:

administering to a human suffering from pains due to the accentuation of the central nerve a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

10. A method for the treatment of pyrexia due to the accentuation of the central nerve, which comprises:
administering to a human suffering from pyrexia due to the accentuation of the central nerve a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

11. A method for the treatment of inflammatory diseases, which comprises:
administering to a human suffering from inflammatory diseases a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

12. A method for the treatment of nephrotic syndrome, which comprises:
administering to a human suffering from nephrotic syndrome a therapeutically effective amount of glycoprotein having a molecular weight of 5000 to 300,000 as determined by ultra-centrifugation and 18 to 38% by weight of proteins, produced by:
(a) culturing a basidiomycetous fungal species belonging to the genus Coriolus;
(b) extracting the thus proliferated mycelia or fruit bodies with hot water or an aqueous alkaline solution; and
(c) removing low molecular weight substances having a molecular weight of less than 5000 from the extract.

13. The method of any one of claims 3-12, wherein said fungal species of the genus Coriolus is the strain *Coriolus versicolor* (Fr.) Quél. identified by ATCC No. 20547.

* * * * *

UNITED STATES PATENT AND TRADEMARK OFFICE
CERTIFICATE OF CORRECTION

PATENT NO. : 5,008,243

DATED : APRIL 16, 91

INVENTOR(S) : MASANORI IKUZAWA ET AL

It is certified that error appears in the above-identified patent and that said Letters Patent is hereby corrected as shown below:

<u>Col.</u> <u>Line</u>

25, 43, delete "strand" and insert --strain--.

Signed and Sealed this

Ninth Day of February, 1993

*Attest:*

STEPHEN G. KUNIN

*Attesting Officer*      *Acting Commissioner of Patents and Trademarks*